US012562252B2

(12) United States Patent
Bryant et al.

(10) Patent No.: US 12,562,252 B2
(45) Date of Patent: *Feb. 24, 2026

(54) SYSTEM AND METHOD FOR ADMINISTERING AN INFUSIBLE FLUID

(71) Applicant: DEKA Products Limited Partnership, Manchester, NH (US)

(72) Inventors: Robert J. Bryant, Manchester, NH (US); Marc A. Mandro, Bow, NH (US)

(73) Assignee: DEKA PRODUCTS LIMITED PARTNERSHIP, Manchester, NH (US)

( * ) Notice: Subject to any disclaimer, the term of this patent is extended or adjusted under 35 U.S.C. 154(b) by 61 days.

This patent is subject to a terminal disclaimer.

(21) Appl. No.: 18/446,585

(22) Filed: Aug. 9, 2023

(65) Prior Publication Data

US 2023/0386638 A1     Nov. 30, 2023

Related U.S. Application Data

(63) Continuation of application No. 16/556,399, filed on Aug. 30, 2019, now Pat. No. 11,763,926, which is a
(Continued)

(51) Int. Cl.
*A61M 5/14*          (2006.01)
*A61M 5/145*         (2006.01)
(Continued)

(52) U.S. Cl.
CPC .......... *G16H 20/17* (2018.01); *A61M 5/1452* (2013.01); *A61M 5/168* (2013.01); *A61M 2005/14208* (2013.01); *A61M 2230/201* (2013.01)

(58) Field of Classification Search
CPC ...... A61M 2005/14208; A61M 5/1723; A61M 2005/14296; A61M 2205/52;
(Continued)

(56) References Cited

U.S. PATENT DOCUMENTS

| 115,917 | A | 6/1871 | Wharton |
| 3,623,474 | A | 11/1971 | Heilman et al. |

(Continued)

FOREIGN PATENT DOCUMENTS

| DE | 4329229 A1 | 3/1995 |
| DE | 19627619 A1 | 1/1998 |

(Continued)

OTHER PUBLICATIONS

U.S. Appl. No. 12/249,636, filed Oct. 10, 2008.
(Continued)

*Primary Examiner* — William R Carpenter
(74) *Attorney, Agent, or Firm* — McCormick, Paulding & Huber PLLC

(57)          ABSTRACT

A method, computer program product, and infusion pump assembly for administering a sequential, multi-part, infusion event, wherein the sequential, multi-part, infusion event includes a plurality of discrete infusion events. If a one-time infusion event is available to be administered, the administration of at least a portion of the plurality of discrete infusion events included within the sequential, multi-part, infusion event is delayed. The one-time infusion event is administered.

5 Claims, 4 Drawing Sheets

Related U.S. Application Data continuation of application No. 14/935,874, filed on Nov. 9, 2015, now Pat. No. 10,398,835, which is a continuation of application No. 12/249,636, filed on Oct. 10, 2008, now Pat. No. 9,180,245.

(51) Int. Cl.
| | |
|---|---|
| *A61M 5/168* | (2006.01) |
| *G16H 20/17* | (2018.01) |
| *A61M 5/142* | (2006.01) |

(58) Field of Classification Search
CPC ...... A61M 2005/1405; A61M 2205/50; A61M 5/16827; G06F 19/3456; G06F 19/3468; G06F 19/3406
See application file for complete search history.

(56) References Cited

U.S. PATENT DOCUMENTS

| | | | |
|---|---|---|---|
| 3,631,847 A | 1/1972 | Hobbs | |
| 3,692,027 A | 9/1972 | Ellinwood, Jr. | |
| 3,752,510 A | 8/1973 | Windischman et al. | |
| 3,811,121 A | 5/1974 | Heim et al. | |
| 3,811,122 A | 5/1974 | Raber et al. | |
| 3,837,339 A | 9/1974 | Aisenberg et al. | |
| 3,887,393 A | 6/1975 | La Rue, Jr. | |
| 3,951,147 A | 4/1976 | Tucker et al. | |
| D248,873 S | 8/1978 | Raitto | |
| 4,123,631 A | 10/1978 | Lewis | |
| 4,146,029 A * | 3/1979 | Ellinwood, Jr. ... | A61N 1/37211 607/9 |
| 4,150,672 A | 4/1979 | Whitney et al. | |
| D254,446 S | 3/1980 | Raitto | |
| 4,206,274 A | 6/1980 | Peels | |
| 4,215,701 A | 8/1980 | Raitto | |
| 4,267,836 A | 5/1981 | Whitney et al. | |
| 4,269,908 A | 5/1981 | Stemme | |
| 4,270,532 A | 6/1981 | Franetzki et al. | |
| 4,273,121 A | 6/1981 | Jassawalla | |
| 4,282,872 A | 8/1981 | Franetzki et al. | |
| 4,296,949 A | 10/1981 | Muetterties et al. | |
| 4,331,262 A | 5/1982 | Snyder et al. | |
| 4,371,594 A | 2/1983 | Ohara et al. | |
| 4,373,527 A | 2/1983 | Fischell | |
| 4,391,883 A | 7/1983 | Williamson et al. | |
| 4,392,847 A | 7/1983 | Whitney et al. | |
| 4,392,849 A | 7/1983 | Petre et al. | |
| 4,395,259 A | 7/1983 | Prestele et al. | |
| 4,437,859 A | 3/1984 | Whitehouse et al. | |
| 4,443,218 A | 4/1984 | Decant, Jr. et al. | |
| 4,464,170 A | 8/1984 | Clemens et al. | |
| 4,468,439 A | 8/1984 | Ohara et al. | |
| 4,469,481 A | 9/1984 | Kobayashi | |
| 4,475,901 A | 10/1984 | Kraegen et al. | |
| 4,493,704 A | 1/1985 | Beard et al. | |
| 4,494,950 A | 1/1985 | Fischell | |
| 4,498,843 A | 2/1985 | Schneider et al. | |
| 4,503,494 A | 3/1985 | Hamilton et al. | |
| 4,529,401 A | 7/1985 | Leslie et al. | |
| 4,533,346 A | 8/1985 | Cosgrove, Jr. et al. | |
| 4,542,532 A | 9/1985 | Mcquilkin | |
| 4,543,093 A | 9/1985 | Christinger | |
| 4,550,731 A | 11/1985 | Batina et al. | |
| 4,559,037 A | 12/1985 | Franetzki et al. | |
| 4,559,038 A | 12/1985 | Berg | |
| 4,561,856 A | 12/1985 | Cochran | |
| 4,562,751 A | 1/1986 | Nason | |
| 4,596,575 A | 6/1986 | Rosenberg | |
| 4,601,707 A | 7/1986 | Albisser | |
| 4,624,661 A | 11/1986 | Arimond | |
| 4,633,878 A | 1/1987 | Bombardieri | |
| 4,648,872 A | 3/1987 | Kamen | |
| 4,673,396 A | 6/1987 | Urbaniak | |
| 4,678,408 A | 7/1987 | Nason | |
| 4,685,902 A | 8/1987 | Edwards | |
| 4,685,903 A | 8/1987 | Cable | |
| 4,690,878 A | 9/1987 | Nakamura | |
| 4,693,684 A | 9/1987 | Blatherwick et al. | |
| 4,696,671 A | 9/1987 | Epstein | |
| 4,714,463 A | 12/1987 | Archibald | |
| 4,731,051 A | 3/1988 | Fischell | |
| 4,731,726 A | 3/1988 | Allen, III | |
| 4,735,441 A | 4/1988 | Stephens | |
| 4,743,895 A | 5/1988 | Alexander | |
| 4,747,828 A | 5/1988 | Tseo | |
| 4,790,028 A | 12/1988 | Ramage | |
| 4,803,625 A | 2/1989 | Fu | |
| 4,804,368 A | 2/1989 | Skakoon | |
| 4,809,697 A | 3/1989 | Causey, III | |
| D301,021 S | 5/1989 | Dommerud | |
| 4,826,810 A | 5/1989 | Aoki | |
| 4,834,712 A | 5/1989 | Quinn | |
| 4,849,852 A | 7/1989 | Mullins | |
| 4,856,340 A | 8/1989 | Garrison | |
| 4,871,351 A | 10/1989 | Feingold | |
| 4,880,712 A | 11/1989 | Gordecki | |
| 4,881,063 A | 11/1989 | Fawcett | |
| 4,898,578 A | 2/1990 | Rubalcaba, Jr. | |
| 4,919,650 A | 4/1990 | Feingold et al. | |
| 4,954,000 A | 9/1990 | Gueret | |
| 4,959,640 A | 9/1990 | Hall | |
| 4,972,508 A | 11/1990 | King | |
| 4,988,337 A | 1/1991 | Ito | |
| 4,997,423 A | 3/1991 | Okuda | |
| 5,009,646 A | 4/1991 | Sudo | |
| 5,019,974 A | 5/1991 | Beckers | |
| 5,034,004 A | 7/1991 | Crankshaw | |
| 5,049,141 A | 9/1991 | Olive | |
| 5,050,612 A | 9/1991 | Matsumura | |
| 5,055,830 A | 10/1991 | Cousins | |
| 5,063,291 A | 11/1991 | Buehring | |
| 5,078,683 A | 1/1992 | Sancoff | |
| 5,080,653 A | 1/1992 | Voss | |
| 5,088,981 A | 2/1992 | Howson | |
| 5,101,814 A | 4/1992 | Palti | |
| 5,102,388 A | 4/1992 | Richmond | |
| 5,103,216 A | 4/1992 | Sisselman | |
| 5,104,374 A | 4/1992 | Bishko | |
| 5,150,314 A | 9/1992 | Garratt | |
| 5,153,827 A | 10/1992 | Coutre | |
| 5,165,407 A | 11/1992 | Wilson | |
| 5,174,716 A | 12/1992 | Hora | |
| 5,176,502 A | 1/1993 | Sanderson | |
| 5,176,644 A | 1/1993 | Srisathapat | |
| 5,176,662 A | 1/1993 | Bartholomew | |
| 5,181,910 A | 1/1993 | Scanlon | |
| 5,187,746 A | 2/1993 | Narisawa | |
| 5,191,855 A | 3/1993 | Conforti | |
| 5,197,322 A | 3/1993 | Indravudh | |
| 5,197,895 A | 3/1993 | Stupecky | |
| 5,205,819 A | 4/1993 | Ross | |
| 5,207,642 A | 5/1993 | Orkin | |
| 5,216,597 A | 6/1993 | Beckers | |
| 5,217,442 A | 6/1993 | Davis | |
| 5,236,416 A | 8/1993 | Mcdaniel et al. | |
| 5,248,569 A | 9/1993 | Pine et al. | |
| 5,254,093 A | 10/1993 | Bartlett et al. | |
| 5,254,096 A | 10/1993 | Rondelet et al. | |
| 5,257,971 A | 11/1993 | Lord et al. | |
| 5,257,980 A | 11/1993 | Van Antwerp et al. | |
| 5,270,702 A | 12/1993 | Krolak | |
| 5,290,639 A | 3/1994 | Mallory | |
| 5,304,152 A | 4/1994 | Sams | |
| 5,307,263 A | 4/1994 | Brown | |
| 5,314,416 A | 5/1994 | Lewis et al. | |
| 5,317,506 A | 5/1994 | Coutre et al. | |
| 5,337,215 A | 8/1994 | Sunderland et al. | |
| 5,338,157 A | 8/1994 | Blomquist | |
| 5,339,821 A | 8/1994 | Fujimoto | |
| 5,341,291 A | 8/1994 | Roizen et al. | |
| 5,342,324 A | 8/1994 | Tucker | |
| 5,349,852 A | 9/1994 | Kamen et al. | |
| 5,350,411 A | 9/1994 | Ryan et al. | |

(56)                    References Cited

U.S. PATENT DOCUMENTS

| | | |
|---|---|---|
| 5,357,427 A | 10/1994 | Langen et al. |
| 5,364,242 A | 11/1994 | Olsen |
| 5,364,346 A | 11/1994 | Schrezenmeir |
| 5,368,562 A | 11/1994 | Blomquist et al. |
| 5,370,622 A | 12/1994 | Livingston et al. |
| 5,372,133 A | 12/1994 | Hogen Esch |
| 5,376,070 A | 12/1994 | Purvis et al. |
| 5,378,231 A | 1/1995 | Johnson et al. |
| 5,383,865 A | 1/1995 | Michel |
| 5,389,078 A | 2/1995 | Zalesky et al. |
| 5,390,671 A | 2/1995 | Lord et al. |
| 5,391,157 A | 2/1995 | Harris et al. |
| 5,399,823 A | 3/1995 | Mccusker |
| 5,403,648 A | 4/1995 | Chan |
| 5,405,614 A | 4/1995 | D'angelo |
| 5,417,667 A | 5/1995 | Tennican et al. |
| 5,429,602 A | 7/1995 | Hauser |
| 5,433,710 A | 7/1995 | Vanantwerp |
| 5,450,003 A | 9/1995 | Cheon |
| 5,456,940 A | 10/1995 | Funderburk |
| 5,460,618 A | 10/1995 | Harreld |
| 5,462,525 A | 10/1995 | Srisathapat et al. |
| 5,464,392 A | 11/1995 | Epstein |
| 5,466,218 A | 11/1995 | Srisathapat et al. |
| 5,472,317 A | 12/1995 | Field et al. |
| 5,476,460 A | 12/1995 | Montalvo |
| 5,478,211 A | 12/1995 | Dominiak et al. |
| 5,482,446 A | 1/1996 | Williamson et al. |
| 5,497,772 A | 3/1996 | Schulman et al. |
| 5,505,709 A | 4/1996 | Funderburk et al. |
| 5,507,727 A | 4/1996 | Crainich |
| 5,508,690 A | 4/1996 | Shur et al. |
| 5,514,097 A | 5/1996 | Knauer |
| 5,522,803 A | 6/1996 | Teissen-simony |
| 5,526,844 A | 6/1996 | Kamen et al. |
| 5,527,307 A | 6/1996 | Srisathapat et al. |
| 5,528,359 A | 6/1996 | Taguchi |
| 5,531,697 A | 7/1996 | Olsen et al. |
| 5,531,698 A | 7/1996 | Olsen |
| 5,533,389 A | 7/1996 | Kamen et al. |
| 5,533,981 A | 7/1996 | Mandro et al. |
| 5,533,996 A | 7/1996 | Murphey et al. |
| 5,538,399 A | 7/1996 | Johnson |
| 5,540,564 A | 7/1996 | Klopfer |
| 5,543,588 A | 8/1996 | Bisset et al. |
| 5,545,140 A | 8/1996 | Conero et al. |
| 5,545,142 A | 8/1996 | Stephens et al. |
| 5,545,143 A | 8/1996 | Fischell |
| 5,545,152 A | 8/1996 | Funderburk et al. |
| 5,558,640 A | 9/1996 | Pfeiler et al. |
| 5,558,641 A | 9/1996 | Glantz et al. |
| 5,562,618 A | 10/1996 | Cai et al. |
| 5,564,915 A | 10/1996 | Johnson |
| 5,567,119 A | 10/1996 | Johnson |
| 5,567,136 A | 10/1996 | Johnson |
| 5,569,026 A | 10/1996 | Novak |
| 5,569,186 A | 10/1996 | Lord et al. |
| 5,569,187 A | 10/1996 | Kaiser |
| 5,573,506 A | 11/1996 | Vasko |
| 5,575,310 A | 11/1996 | Kamen et al. |
| 5,582,593 A | 12/1996 | Hultman |
| 5,584,813 A | 12/1996 | Livingston et al. |
| 5,593,390 A | 1/1997 | Castellano et al. |
| 5,594,638 A | 1/1997 | Iliff |
| 5,609,060 A | 3/1997 | Dent |
| 5,609,575 A | 3/1997 | Larson et al. |
| 5,613,945 A | 3/1997 | Cai et al. |
| 5,620,312 A | 4/1997 | Hyman et al. |
| 5,626,144 A | 5/1997 | Tacklind et al. |
| 5,630,710 A | 5/1997 | Tune et al. |
| 5,632,315 A | 5/1997 | Rose |
| 5,632,729 A | 5/1997 | Cai et al. |
| 5,637,095 A | 6/1997 | Nason et al. |
| 5,637,420 A | 6/1997 | Jones, Jr. et al. |
| 5,641,892 A | 6/1997 | Larkins et al. |
| 5,643,212 A | 7/1997 | Coutre et al. |
| 5,647,853 A | 7/1997 | Feldmann et al. |
| 5,647,854 A | 7/1997 | Olsen et al. |
| 5,651,775 A | 7/1997 | Walker et al. |
| 5,658,133 A | 8/1997 | Anderson et al. |
| 5,658,250 A | 8/1997 | Blomquist et al. |
| 5,658,252 A | 8/1997 | Johnson |
| 5,660,176 A | 8/1997 | Iliff |
| 5,665,065 A | 9/1997 | Colman et al. |
| 5,669,877 A | 9/1997 | Blomquist |
| 5,669,887 A | 9/1997 | Cooper |
| 5,678,568 A | 10/1997 | Uchikubo et al. |
| 5,681,285 A | 10/1997 | Ford et al. |
| 5,685,844 A | 11/1997 | Marttila |
| 5,687,734 A | 11/1997 | Dempsey et al. |
| 5,695,473 A | 12/1997 | Olsen |
| 5,704,366 A | 1/1998 | Tacklind et al. |
| 5,712,795 A | 1/1998 | Layman et al. |
| 5,713,856 A | 2/1998 | Eggers et al. |
| 5,713,857 A | 2/1998 | Grimard et al. |
| 5,716,725 A | 2/1998 | Riveron et al. |
| 5,718,562 A | 2/1998 | Lawless et al. |
| 5,720,729 A | 2/1998 | Kriesel |
| 5,727,241 A | 3/1998 | Yamano et al. |
| 5,733,673 A | 3/1998 | Kunert |
| 5,743,873 A | 4/1998 | Cai et al. |
| 5,752,940 A | 5/1998 | Grimard |
| 5,755,744 A | 5/1998 | Shaw et al. |
| 5,762,632 A | 6/1998 | Whisson |
| 5,764,159 A | 6/1998 | Neftel |
| 5,772,409 A | 6/1998 | Johnson |
| 5,772,635 A | 6/1998 | Dastur et al. |
| 5,776,116 A | 7/1998 | Lopez et al. |
| 5,779,665 A | 7/1998 | Mastrototaro et al. |
| 5,785,681 A | 7/1998 | Indravudh |
| 5,788,669 A | 8/1998 | Peterson |
| 5,788,671 A | 8/1998 | Johnson |
| 5,788,673 A | 8/1998 | Young et al. |
| 5,788,678 A | 8/1998 | Van Antwerp |
| 5,795,337 A | 8/1998 | Grimard |
| 5,800,387 A | 9/1998 | Duffy et al. |
| 5,800,420 A | 9/1998 | Gross et al. |
| 5,801,600 A | 9/1998 | Butland et al. |
| 5,807,336 A | 9/1998 | Russo et al. |
| 5,810,001 A | 9/1998 | Genga et al. |
| 5,810,771 A | 9/1998 | Blomquist |
| 5,814,015 A | 9/1998 | Gargano et al. |
| 5,822,715 A | 10/1998 | Worthington et al. |
| 5,823,746 A | 10/1998 | Johnson |
| 5,832,448 A | 11/1998 | Brown |
| 5,840,020 A | 11/1998 | Heinonen et al. |
| 5,840,026 A | 11/1998 | Uber, III et al. |
| 5,843,146 A | 12/1998 | Cross, Jr. |
| 5,851,197 A | 12/1998 | Marano |
| 5,851,692 A | 12/1998 | Potts |
| 5,861,018 A | 1/1999 | Feierbach |
| 5,868,669 A | 2/1999 | Iliff |
| 5,871,465 A | 2/1999 | Vasko |
| 5,876,370 A | 3/1999 | Blomquist |
| 5,879,143 A | 3/1999 | Cote |
| 5,879,144 A | 3/1999 | Johnson |
| 5,879,163 A | 3/1999 | Brown |
| 5,882,047 A | 3/1999 | Ostrander |
| 5,882,256 A | 3/1999 | Shropshire |
| 5,885,245 A | 3/1999 | Lynch |
| 5,897,493 A | 4/1999 | Brown |
| 5,899,855 A | 5/1999 | Brown |
| 5,913,310 A | 6/1999 | Brown |
| 5,918,603 A | 7/1999 | Brown |
| 5,925,021 A | 7/1999 | Castellano |
| 5,928,196 A | 7/1999 | Johnson |
| 5,928,202 A | 7/1999 | Linnebjerg |
| 5,931,791 A | 8/1999 | Saltzstein |
| 5,933,136 A | 8/1999 | Brown |
| 5,935,099 A | 8/1999 | Peterson |
| 5,935,105 A | 8/1999 | Manning |
| 5,935,106 A | 8/1999 | Olsen |
| 5,940,801 A | 8/1999 | Brown |
| 5,951,521 A | 9/1999 | Mastrototaro |

(56) References Cited

U.S. PATENT DOCUMENTS

| | | | |
|---|---|---|---|
| 5,954,485 A | 9/1999 | Johnson |
| 5,954,697 A | 9/1999 | Srisathapat |
| 5,954,700 A | 9/1999 | Kovelman |
| 5,956,501 A | 9/1999 | Brown |
| 5,957,890 A | 9/1999 | Mann |
| 5,960,403 A | 9/1999 | Brown |
| 5,968,011 A | 10/1999 | Larsen |
| 5,971,963 A | 10/1999 | Choi |
| 5,973,623 A | 10/1999 | Gupta et al. |
| 5,980,506 A | 11/1999 | Mathiasen |
| 5,989,216 A | 11/1999 | Johnson et al. |
| 5,989,227 A | 11/1999 | Vetter et al. |
| 5,997,476 A | 12/1999 | Brown |
| 6,007,941 A | 12/1999 | Hermann et al. |
| 6,009,339 A | 12/1999 | Bentsen et al. |
| 6,014,587 A | 1/2000 | Shaw et al. |
| 6,017,326 A | 1/2000 | Pasqualucci et al. |
| 6,017,328 A | 1/2000 | Fischell et al. |
| 6,024,539 A | 2/2000 | Blomquist |
| 6,032,119 A | 2/2000 | Brown et al. |
| 6,042,565 A | 3/2000 | Hirschman et al. |
| 6,043,610 A | 3/2000 | Buell |
| 6,056,522 A | 5/2000 | Johnson |
| 6,056,718 A | 5/2000 | Funderburk et al. |
| 6,057,169 A | 5/2000 | Singh et al. |
| 6,059,753 A | 5/2000 | Faust et al. |
| 6,063,059 A | 5/2000 | Kriesel |
| 6,067,474 A | 5/2000 | Schulman et al. |
| 6,073,036 A | 6/2000 | Heikkinen et al. |
| 6,077,055 A | 6/2000 | Vilks |
| 6,086,575 A | 7/2000 | Mejslov |
| 6,090,071 A | 7/2000 | Kriesel |
| 6,090,081 A | 7/2000 | Sudo et al. |
| 6,093,172 A | 7/2000 | Funderburk et al. |
| 6,096,011 A | 8/2000 | Trombley, III et al. |
| 6,099,507 A | 8/2000 | Heinzerling |
| 6,101,478 A | 8/2000 | Brown |
| 6,110,152 A | 8/2000 | Kovelman |
| 6,112,111 A | 8/2000 | Glantz |
| 6,123,686 A | 9/2000 | Olsen |
| 6,123,690 A | 9/2000 | Mejslov |
| 6,135,949 A | 10/2000 | Russo |
| 6,142,150 A | 11/2000 | O'mahoney |
| 6,146,109 A | 11/2000 | Davis |
| 6,165,154 A | 12/2000 | Gray |
| 6,171,287 B1 | 1/2001 | Lynn |
| 6,202,708 B1 | 3/2001 | Bynum |
| 6,206,856 B1 | 3/2001 | Mahurkar |
| 6,211,856 B1 | 4/2001 | Choi |
| 6,216,795 B1 | 4/2001 | Buchl |
| 6,225,711 B1 | 5/2001 | Gupta |
| 6,241,704 B1 | 6/2001 | Peterson |
| 6,246,992 B1 | 6/2001 | Brown |
| 6,248,093 B1 | 6/2001 | Moberg |
| 6,253,804 B1 | 7/2001 | Safabash |
| 6,254,586 B1 | 7/2001 | Mann |
| 6,259,587 B1 | 7/2001 | Sheldon |
| 6,267,564 B1 | 7/2001 | Rapheal |
| 6,269,340 B1 | 7/2001 | Ford |
| 6,270,455 B1 | 8/2001 | Brown |
| 6,280,416 B1 | 8/2001 | Van Antwerp |
| 6,283,943 B1 | 9/2001 | Dy |
| 6,283,949 B1 | 9/2001 | Roorda |
| 6,293,159 B1 | 9/2001 | Kriesel |
| 6,293,925 B1 | 9/2001 | Safabash |
| 6,305,908 B1 | 10/2001 | Hermann |
| 6,309,375 B1 | 10/2001 | Glines |
| 6,311,868 B1 | 11/2001 | Krietemeier |
| 6,321,158 B1 | 11/2001 | Delorme et al. |
| 6,336,913 B1 | 1/2002 | Spohn et al. |
| 6,362,591 B1 | 3/2002 | Moberg |
| 6,364,859 B1 | 4/2002 | Romain et al. |
| 6,364,865 B1 | 4/2002 | Lavi et al. |
| 6,374,876 B2 | 4/2002 | Bynum |
| 6,375,638 B2 | 4/2002 | Nason et al. |
| 6,416,293 B1 | 7/2002 | Bouchard et al. |
| 6,422,057 B1 | 7/2002 | Anderson |
| 6,423,035 B1 | 7/2002 | Das et al. |
| 6,427,088 B1 | 7/2002 | Bowman, IV et al. |
| 6,428,509 B1 | 8/2002 | Fielder |
| 6,447,481 B1 | 9/2002 | Duchon et al. |
| 6,453,956 B2 | 9/2002 | Safabash |
| 6,458,102 B1 | 10/2002 | Mann et al. |
| 6,459,424 B1 | 10/2002 | Resman |
| 6,461,329 B1 | 10/2002 | Van Antwerp et al. |
| 6,461,331 B1 | 10/2002 | Van Antwerp |
| 6,466,203 B2 | 10/2002 | Van Ee |
| 6,475,180 B2 | 11/2002 | Peterson et al. |
| 6,475,196 B1 | 11/2002 | Vachon |
| 6,485,461 B1 | 11/2002 | Mason et al. |
| 6,485,465 B2 | 11/2002 | Moberg et al. |
| 6,488,663 B1 | 12/2002 | Steg |
| 6,520,938 B1 | 2/2003 | Funderburk et al. |
| 6,537,268 B1 | 3/2003 | Gibson et al. |
| 6,549,423 B1 | 4/2003 | Brodnick |
| 6,551,276 B1 | 4/2003 | Mann et al. |
| 6,551,277 B1 | 4/2003 | Ford |
| 6,554,798 B1 | 4/2003 | Mann et al. |
| 6,554,800 B1 | 4/2003 | Nezhadian et al. |
| 6,555,986 B2 | 4/2003 | Moberg |
| 6,558,320 B1 | 5/2003 | Causey, III et al. |
| 6,558,361 B1 | 5/2003 | Yeshurun |
| 6,562,001 B2 | 5/2003 | Lebel et al. |
| 6,562,023 B1 | 5/2003 | Marrs et al. |
| 6,564,105 B2 | 5/2003 | Starkweather et al. |
| 6,571,128 B2 | 5/2003 | Lebel et al. |
| 6,572,542 B1 | 6/2003 | Houben et al. |
| 6,572,585 B2 | 6/2003 | Choi |
| 6,572,586 B1 | 6/2003 | Wojcik |
| 6,577,899 B2 | 6/2003 | Lebel et al. |
| 6,579,267 B2 | 6/2003 | Lynch et al. |
| RE38,189 E | 7/2003 | Walker et al. |
| 6,585,644 B2 | 7/2003 | Lebel et al. |
| 6,585,695 B1 | 7/2003 | Adair et al. |
| 6,591,876 B2 | 7/2003 | Safabash |
| 6,592,551 B1 | 7/2003 | Cobb |
| 6,595,756 B2 | 7/2003 | Gray et al. |
| 6,607,509 B2 | 8/2003 | Bobroff et al. |
| 6,611,410 B1 | 8/2003 | Makaran |
| 6,613,015 B2 | 9/2003 | Sandstrom et al. |
| D480,477 S | 10/2003 | Bush et al. |
| 6,641,533 B2 | 11/2003 | Causey, III et al. |
| 6,642,936 B1 | 11/2003 | Engholm et al. |
| 6,645,177 B1 | 11/2003 | Shearn |
| 6,648,821 B2 | 11/2003 | Lebel et al. |
| 6,652,493 B1 | 11/2003 | Das |
| 6,652,510 B2 | 11/2003 | Lord et al. |
| 6,656,148 B2 | 12/2003 | Das et al. |
| 6,656,158 B2 | 12/2003 | Gregory et al. |
| 6,656,159 B2 | 12/2003 | Flaherty |
| 6,659,948 B2 | 12/2003 | Lebel et al. |
| 6,665,909 B2 | 12/2003 | Collins et al. |
| 6,669,669 B2 | 12/2003 | Flaherty et al. |
| 6,684,058 B1 | 1/2004 | Karacaoglu et al. |
| 6,685,674 B2 | 2/2004 | Douglas et al. |
| 6,685,678 B2 | 2/2004 | Evans et al. |
| 6,687,546 B2 | 2/2004 | Lebel et al. |
| 6,689,091 B2 | 2/2004 | Bui et al. |
| 6,691,043 B2 | 2/2004 | Ribeiro, Jr. |
| 6,692,457 B2 | 2/2004 | Flaherty |
| 6,694,191 B2 | 2/2004 | Starkweather et al. |
| 6,699,218 B2 | 3/2004 | Flaherty et al. |
| 6,704,034 B1 | 3/2004 | Rodriguez et al. |
| 6,716,195 B2 | 4/2004 | Nolan, Jr. et al. |
| 6,723,072 B2 | 4/2004 | Mahoney et al. |
| 6,733,446 B2 | 5/2004 | Lebel et al. |
| 6,738,671 B2 | 5/2004 | Christophersom et al. |
| 6,740,059 B2 | 5/2004 | Flaherty |
| 6,740,072 B2 | 5/2004 | Starkweather et al. |
| 6,740,075 B2 | 5/2004 | Lebel et al. |
| 6,743,205 B2 | 6/2004 | Nolan, Jr. et al. |
| 6,744,350 B2 | 6/2004 | Blomquist |
| 6,749,586 B2 | 6/2004 | Vasko |
| 6,749,587 B2 | 6/2004 | Flaherty |

(56)  References Cited

U.S. PATENT DOCUMENTS

| | | | |
|---|---|---|---|
| 6,752,299 B2 | 6/2004 | Shetler et al. |
| 6,752,785 B2 | 6/2004 | Van Antwerp et al. |
| 6,752,787 B1 | 6/2004 | Causey, III et al. |
| 6,752,789 B2 | 6/2004 | Duchon et al. |
| 6,755,220 B2 | 6/2004 | Castellano et al. |
| 6,757,630 B2 | 6/2004 | Mcclendon et al. |
| 6,758,810 B2 | 7/2004 | Lebel et al. |
| 6,768,425 B2 | 7/2004 | Flaherty et al. |
| 6,770,067 B2 | 8/2004 | Lorenzen et al. |
| 6,772,650 B2 | 8/2004 | Biwa et al. |
| 6,796,957 B2 | 9/2004 | Carpenter et al. |
| 6,800,071 B1 | 10/2004 | Mcconnell et al. |
| 6,801,420 B2 | 10/2004 | Talbot et al. |
| 6,804,558 B2 | 10/2004 | Haller et al. |
| 6,805,693 B2 | 10/2004 | Gray et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,817,990 B2 | 11/2004 | Yap et al. |
| 6,827,702 B2 | 12/2004 | Lebel et al. |
| 6,830,558 B2 | 12/2004 | Flaherty et al. |
| 6,835,190 B2 | 12/2004 | Nguyen |
| 6,845,465 B2 | 1/2005 | Hashemi |
| 6,852,104 B2 | 2/2005 | Blomquist |
| 6,854,620 B2 | 2/2005 | Ramey |
| 6,872,200 B2 | 3/2005 | Mann et al. |
| 6,873,268 B2 | 3/2005 | Lebel et al. |
| 6,879,930 B2 | 4/2005 | Sinclair et al. |
| 6,887,216 B2 | 5/2005 | Hochman et al. |
| 6,902,207 B2 | 6/2005 | Lickliter |
| 6,904,324 B2 | 6/2005 | Bishay |
| 6,916,010 B2 | 7/2005 | Beck et al. |
| 6,930,602 B2 | 8/2005 | Villaseca et al. |
| 6,932,584 B2 | 8/2005 | Gray et al. |
| 6,936,029 B2 | 8/2005 | Mann et al. |
| 6,945,760 B2 | 9/2005 | Gray et al. |
| 6,950,708 B2 | 9/2005 | Bowman IV et al. |
| 6,951,551 B2 | 10/2005 | Hudon |
| 6,958,705 B2 | 10/2005 | Lebel et al. |
| 6,960,192 B1 | 11/2005 | Flaherty et al. |
| 6,960,195 B2 | 11/2005 | Heinz et al. |
| 6,964,643 B2 | 11/2005 | Hovland et al. |
| 6,974,437 B2 | 12/2005 | Lebel et al. |
| 6,978,182 B2 | 12/2005 | Mazar et al. |
| 6,978,517 B2 | 12/2005 | Collins et al. |
| 6,979,326 B2 | 12/2005 | Mann et al. |
| 6,994,619 B2 | 2/2006 | Scholten |
| 6,997,905 B2 | 2/2006 | Gillespie, Jr. et al. |
| 6,997,907 B2 | 2/2006 | Safabash et al. |
| 6,997,910 B2 | 2/2006 | Howlett et al. |
| 6,997,920 B2 | 2/2006 | Mann et al. |
| 6,997,921 B2 | 2/2006 | Gray et al. |
| 6,999,854 B2 | 2/2006 | Roth |
| 7,011,608 B2 | 3/2006 | Spencer |
| 7,018,360 B2 | 3/2006 | Flaherty et al. |
| 7,018,361 B2 | 3/2006 | Gillespie, Jr. et al. |
| 7,021,560 B2 | 4/2006 | Gray et al. |
| 7,024,245 B2 | 4/2006 | Lebel et al. |
| 7,025,226 B2 | 4/2006 | Ramey |
| 7,025,743 B2 | 4/2006 | Mann et al. |
| 7,025,757 B2 | 4/2006 | Reilly et al. |
| 7,029,455 B2 | 4/2006 | Flaherty |
| 7,029,456 B2 | 4/2006 | Ware et al. |
| 7,033,338 B2 | 4/2006 | Vilks et al. |
| 7,033,339 B1 | 4/2006 | Lynn |
| 7,039,755 B1 | 5/2006 | Helms |
| 7,041,082 B2 | 5/2006 | Blomquist et al. |
| 7,045,361 B2 | 5/2006 | Heiss et al. |
| 7,046,230 B2 | 5/2006 | Zadesky et al. |
| 7,048,691 B2 | 5/2006 | Miele et al. |
| 7,050,927 B2 | 5/2006 | Sinclair et al. |
| 7,052,251 B2 | 5/2006 | Nason et al. |
| 7,052,483 B2 | 5/2006 | Wojcik |
| 7,061,140 B2 | 6/2006 | Zhang et al. |
| 7,063,684 B2 | 6/2006 | Moberg |
| 7,066,029 B2 | 6/2006 | Beavis et al. |
| 7,074,209 B2 | 7/2006 | Evans et al. |
| 7,075,512 B1 | 7/2006 | Fabre et al. |
| 7,088,343 B2 | 8/2006 | Smith et al. |
| 7,098,803 B2 | 8/2006 | Mann et al. |
| 7,109,878 B2 | 9/2006 | Mann et al. |
| 7,113,821 B1 | 9/2006 | Sun et al. |
| 7,115,113 B2 | 10/2006 | Evans et al. |
| 7,125,395 B2 | 10/2006 | Hommann et al. |
| 7,131,967 B2 | 11/2006 | Gray et al. |
| 7,137,964 B2 | 11/2006 | Flaherty |
| 7,144,384 B2 | 12/2006 | Gorman et al. |
| 7,146,977 B2 | 12/2006 | Beavis et al. |
| 7,150,724 B2 | 12/2006 | Morris et al. |
| 7,150,741 B2 | 12/2006 | Erickson et al. |
| 7,153,288 B2 | 12/2006 | Duchon et al. |
| 7,153,289 B2 | 12/2006 | Vasko |
| 7,158,125 B2 | 1/2007 | Sinclair et al. |
| 7,181,505 B2 | 2/2007 | Haller et al. |
| 7,193,521 B2 | 3/2007 | Moberg et al. |
| 7,204,823 B2 | 4/2007 | Estes et al. |
| 7,211,782 B2 | 5/2007 | Tobiason e |
| 7,226,692 B2 | 6/2007 | Singer et al. |
| 7,263,871 B2 | 9/2007 | Selker et al. |
| 7,273,477 B2 | 9/2007 | Spohn et al. |
| 7,278,983 B2 | 10/2007 | Ireland et al. |
| 7,303,549 B2 | 12/2007 | Flaherty et al. |
| 7,305,984 B2 | 12/2007 | Altobelli et al. |
| 7,306,578 B2 | 12/2007 | Gray et al. |
| 7,329,241 B2 | 2/2008 | Horvath et al. |
| 7,342,660 B2 | 3/2008 | Altobelli et al. |
| 7,344,500 B2 | 3/2008 | Talbot et al. |
| 7,355,595 B2 | 4/2008 | Bathiche et al. |
| 7,390,314 B2 | 6/2008 | Stutz, Jr. et al. |
| 7,394,458 B2 | 7/2008 | Lyon et al. |
| 7,404,796 B2 | 7/2008 | Ginsberg |
| 7,406,683 B2 | 7/2008 | Kalidindi et al. |
| 7,427,002 B2 | 9/2008 | Liff et al. |
| 7,442,186 B2 | 10/2008 | Blomquist |
| 7,470,253 B2 | 12/2008 | Kriesel et al. |
| 7,471,284 B2 | 12/2008 | Bathiche et al. |
| 7,471,994 B2 | 12/2008 | Ford et al. |
| 7,489,105 B2 | 2/2009 | Weinstein et al. |
| 7,498,563 B2 | 3/2009 | Mandro et al. |
| 7,510,544 B2 | 3/2009 | Vilks et al. |
| 7,517,332 B2 | 4/2009 | Tonelli et al. |
| 7,522,744 B2 | 4/2009 | Bai et al. |
| 7,527,052 B2 | 5/2009 | Hickle et al. |
| 7,547,281 B2 | 6/2009 | Hayes et al. |
| 7,559,524 B2 | 7/2009 | Gray et al. |
| 7,566,326 B2 | 7/2009 | Duchon et al. |
| 7,592,740 B2 | 9/2009 | Roe |
| 7,597,682 B2 | 10/2009 | Moberg |
| 7,608,060 B2 | 10/2009 | Gillespie, Jr. et al. |
| 7,621,893 B2 | 11/2009 | Moberg et al. |
| 7,628,772 B2 | 12/2009 | Mcconnell et al. |
| 7,628,782 B2 | 12/2009 | Adair et al. |
| 7,635,349 B2 | 12/2009 | Tribe et al. |
| 7,647,237 B2 | 1/2010 | Malave et al. |
| 7,651,489 B2 | 1/2010 | Estes et al. |
| 7,653,883 B2 | 1/2010 | Hotelling et al. |
| 7,655,351 B2 | 2/2010 | Etter et al. |
| 7,658,734 B2 | 2/2010 | Adair et al. |
| 7,663,607 B2 | 2/2010 | Hotelling et al. |
| 7,682,338 B2 | 3/2010 | Griffin |
| 7,686,787 B2 | 3/2010 | Moberg et al. |
| 7,699,806 B2 | 4/2010 | Ware et al. |
| 7,699,833 B2 | 4/2010 | Moberg et al. |
| 7,704,226 B2 | 4/2010 | Mueller, Jr. et al. |
| 7,704,227 B2 | 4/2010 | Moberg et al. |
| 7,736,344 B2 | 6/2010 | Moberg et al. |
| 7,737,581 B2 | 6/2010 | Spurlin et al. |
| 7,737,953 B2 | 6/2010 | Mackey |
| 7,744,589 B2 | 6/2010 | Mounce et al. |
| 7,766,873 B2 | 8/2010 | Moberg et al. |
| 7,776,029 B2 | 8/2010 | Whitehurst et al. |
| 7,785,288 B2 | 8/2010 | Mernøe et al. |
| 7,794,426 B2 | 9/2010 | Briones et al. |

(56)  References Cited

U.S. PATENT DOCUMENTS

| | | | |
|---|---|---|---|
| 7,794,434 B2 | 9/2010 | Mounce et al. |
| 7,806,868 B2 | 10/2010 | De Polo et al. |
| 7,811,262 B2 | 10/2010 | Moberg et al. |
| 7,815,602 B2 | 10/2010 | Mann et al. |
| 7,819,843 B2 | 10/2010 | Mann et al. |
| 7,828,764 B2 | 11/2010 | Moberg et al. |
| 7,875,022 B2 | 1/2011 | Wenger et al. |
| 7,892,206 B2 | 2/2011 | Moberg et al. |
| 7,905,859 B2 | 3/2011 | Bynum et al. |
| 7,914,483 B2 | 3/2011 | Simmons |
| 7,918,825 B2 | 4/2011 | O'connor et al. |
| 7,922,708 B2 | 4/2011 | Estes et al. |
| 7,927,314 B2 | 4/2011 | Kuracina et al. |
| 7,933,780 B2 | 4/2011 | De La |
| 7,935,104 B2 | 5/2011 | Yodfat et al. |
| 7,938,797 B2 | 5/2011 | Estes |
| 7,942,844 B2 | 5/2011 | Moberg et al. |
| 7,944,366 B2 | 5/2011 | Krulevitch et al. |
| 7,945,452 B2 | 5/2011 | Fathallah et al. |
| 7,963,917 B2 | 6/2011 | Kellogg et al. |
| 7,963,954 B2 | 6/2011 | Kavazov |
| 7,966,391 B2 | 6/2011 | Anderson et al. |
| 7,967,785 B2 | 6/2011 | Morgan et al. |
| 7,967,812 B2 | 6/2011 | Jasperson et al. |
| 7,981,076 B2 | 7/2011 | Sullivan et al. |
| 7,993,108 B2 | 8/2011 | Rush et al. |
| 7,997,304 B2 | 8/2011 | Ranalletta et al. |
| 7,998,122 B2 | 8/2011 | Lynn et al. |
| 8,009,499 B2 | 8/2011 | Reuter et al. |
| 8,016,789 B2 | 9/2011 | Grant et al. |
| 8,017,890 B2 | 9/2011 | Paradiso et al. |
| 8,021,344 B2 | 9/2011 | Edwards et al. |
| 8,032,226 B2 | 10/2011 | Miller et al. |
| 8,034,019 B2 | 10/2011 | Nair et al. |
| 8,034,026 B2 | 10/2011 | Grant et al. |
| 8,105,282 B2 | 1/2012 | Susi et al. |
| 8,108,040 B2 | 1/2012 | Bernard et al. |
| 8,113,244 B2 | 2/2012 | Kamen et al. |
| 8,120,485 B2 | 2/2012 | Yang |
| 8,127,046 B2 | 2/2012 | Grant et al. |
| 8,137,314 B2 | 3/2012 | Mounce et al. |
| 8,147,446 B2 | 4/2012 | Yodfat et al. |
| 8,182,461 B2 | 5/2012 | Pope et al. |
| 8,217,915 B2 | 7/2012 | Philipp |
| 8,226,556 B2 | 7/2012 | Hayes et al. |
| 8,239,784 B2 | 8/2012 | Hotelling et al. |
| 8,262,616 B2 | 9/2012 | Grant et al. |
| 8,267,892 B2 | 9/2012 | Spencer et al. |
| 8,277,415 B2 | 10/2012 | Mounce et al. |
| 8,287,514 B2 | 10/2012 | Miller et al. |
| 8,302,600 B2 | 11/2012 | Andrieux et al. |
| 8,349,174 B2 | 1/2013 | Bedingfield et al. |
| 8,381,135 B2 | 2/2013 | Hotelling et al. |
| 8,390,244 B2 | 3/2013 | Wooley et al. |
| 8,393,323 B2 | 3/2013 | Andrieux et al. |
| 8,398,590 B2 | 3/2013 | Sternberg et al. |
| 8,414,522 B2 | 4/2013 | Kamen et al. |
| 8,444,607 B2 | 5/2013 | Mounce et al. |
| 8,489,427 B2 | 7/2013 | Simpson et al. |
| 8,500,054 B2 | 8/2013 | Grant et al. |
| 8,512,276 B2 | 8/2013 | Talbot et al. |
| 8,518,021 B2 | 8/2013 | Stewart et al. |
| 8,529,553 B2 | 9/2013 | Mounce et al. |
| 8,545,445 B2 | 10/2013 | Kamen et al. |
| 8,579,813 B2 | 11/2013 | Causey, III et al. |
| 8,585,377 B2 | 11/2013 | Kamen et al. |
| 8,617,109 B2 | 12/2013 | Kronestedt et al. |
| 8,626,297 B2 | 1/2014 | Jaax et al. |
| 8,672,876 B2 | 3/2014 | Jacobson et al. |
| 8,721,584 B2 | 5/2014 | Braithwaite et al. |
| 8,728,024 B2 | 5/2014 | Kamen et al. |
| 8,794,929 B2 | 8/2014 | Anex et al. |
| 8,840,586 B2 | 9/2014 | Bente, IV et al. |
| 8,840,587 B2 | 9/2014 | Bente, IV et al. |
| 8,950,396 B2 | 2/2015 | Wachtel et al. |
| 9,081,626 B2 | 7/2015 | Hedley et al. |
| 9,173,996 B2 | 11/2015 | Gray et al. |
| 9,180,245 B2 * | 11/2015 | Bryant .................. G16H 20/17 |
| 9,348,458 B2 | 5/2016 | Hotelling et al. |
| 9,552,053 B2 | 1/2017 | O'connor et al. |
| 9,713,701 B2 | 7/2017 | Sarkar et al. |
| 9,833,569 B2 | 12/2017 | Gray et al. |
| 9,878,103 B2 | 1/2018 | Guillermo et al. |
| 9,968,742 B2 | 5/2018 | Van Antwerp et al. |
| 10,154,804 B2 | 12/2018 | Steil et al. |
| 10,207,048 B2 | 2/2019 | Gray et al. |
| 10,398,835 B2 * | 9/2019 | Bryant .................. G16H 20/17 |
| 11,763,926 B2 * | 9/2023 | Bryant ................ A61M 5/1452 |
| | | | 604/890.1 |
| 2001/0041869 A1 | 11/2001 | Causey, III et al. |
| 2002/0052539 A1 | 5/2002 | Haller et al. |
| 2002/0056114 A1 | 5/2002 | Fillebrown et al. |
| 2002/0120231 A1 | 8/2002 | Douglas et al. |
| 2002/0161332 A1 | 10/2002 | Ramey |
| 2002/0173748 A1 | 11/2002 | Mcconnell et al. |
| 2002/0193846 A1 | 12/2002 | Pool et al. |
| 2003/0065308 A1 | 4/2003 | Lebel et al. |
| 2003/0088238 A1 | 5/2003 | Poulsen et al. |
| 2003/0132922 A1 | 7/2003 | Philipp |
| 2003/0141981 A1 | 7/2003 | Bui et al. |
| 2003/0163089 A1 | 8/2003 | Bynum |
| 2003/0212379 A1 | 11/2003 | Bylund et al. |
| 2004/0003493 A1 | 1/2004 | Adair et al. |
| 2004/0068230 A1 | 4/2004 | Estes et al. |
| 2004/0073161 A1 | 4/2004 | Tachibana |
| 2004/0092878 A1 | 5/2004 | Flaherty |
| 2004/0133166 A1 | 7/2004 | Moberg et al. |
| 2004/0140304 A1 | 7/2004 | Leyendecker |
| 2004/0158193 A1 | 8/2004 | Bui et al. |
| 2004/0172301 A1 | 9/2004 | Mihai et al. |
| 2004/0176667 A1 | 9/2004 | Mihai et al. |
| 2004/0193090 A1 | 9/2004 | Lebel et al. |
| 2004/0235446 A1 | 11/2004 | Flaherty et al. |
| 2005/0022274 A1 | 1/2005 | Campbell et al. |
| 2005/0055242 A1 | 3/2005 | Bello et al. |
| 2005/0055244 A1 | 3/2005 | Mullan et al. |
| 2005/0063857 A1 | 3/2005 | Alheidt et al. |
| 2005/0065817 A1 | 3/2005 | Mihai et al. |
| 2005/0137530 A1 | 6/2005 | Campbell et al. |
| 2005/0137573 A1 | 6/2005 | Mclaughlin |
| 2005/0171512 A1 | 8/2005 | Flaherty |
| 2005/0177111 A1 | 8/2005 | Ozeri et al. |
| 2005/0182366 A1 | 8/2005 | Vogt et al. |
| 2005/0182389 A1 | 8/2005 | Laporte et al. |
| 2005/0187515 A1 | 8/2005 | Varrichio et al. |
| 2005/0187593 A1 | 8/2005 | Housworth et al. |
| 2005/0215982 A1 | 9/2005 | Malave et al. |
| 2005/0238507 A1 | 10/2005 | Diianni et al. |
| 2005/0242126 A1 | 11/2005 | Izoe |
| 2005/0261660 A1 | 11/2005 | Choi |
| 2005/0267550 A1 | 12/2005 | Hess et al. |
| 2005/0285880 A1 | 12/2005 | Lai et al. |
| 2006/0041229 A1 | 2/2006 | Garibotto et al. |
| 2006/0100591 A1 | 5/2006 | Alheidt et al. |
| 2006/0160670 A1 | 7/2006 | Spencer |
| 2006/0173444 A1 | 8/2006 | Choy et al. |
| 2006/0178633 A1 | 8/2006 | Garibotto et al. |
| 2006/0200257 A1 | 9/2006 | Kirste et al. |
| 2006/0227117 A1 | 10/2006 | Proctor |
| 2006/0232554 A1 | 10/2006 | Wong et al. |
| 2006/0253085 A1 | 11/2006 | Geismar et al. |
| 2006/0282290 A1 | 12/2006 | Flaherty et al. |
| 2007/0060872 A1 | 3/2007 | Hall et al. |
| 2007/0066940 A1 | 3/2007 | Karunaratne et al. |
| 2007/0066956 A1 | 3/2007 | Finkel |
| 2007/0072146 A1 | 3/2007 | Pierson |
| 2007/0093750 A1 | 4/2007 | Jan et al. |
| 2007/0100283 A1 | 5/2007 | Causey et al. |
| 2007/0118405 A1 | 5/2007 | Campbell et al. |
| 2007/0203439 A1 | 8/2007 | Boyd et al. |
| 2007/0244469 A1 | 10/2007 | Ozeri et al. |
| 2007/0258395 A1 | 11/2007 | Jollota et al. |
| 2008/0125700 A1 | 5/2008 | Moberg et al. |
| 2008/0160492 A1 | 7/2008 | Campbell et al. |

(56)                  References Cited

U.S. PATENT DOCUMENTS

| 2008/0161754 | A1 | 7/2008 | Marano-ford |
| 2008/0215029 | A1 | 9/2008 | Rake et al. |
| 2009/0062778 | A1 | 3/2009 | Bengtsson et al. |
| 2009/0118683 | A1 | 5/2009 | Hanson et al. |
| 2009/0163855 | A1 | 6/2009 | Shin et al. |
| 2009/0164251 | A1 | 6/2009 | Hayter |
| 2009/0172425 | A1 | 7/2009 | Cetin et al. |
| 2009/0198183 | A1 | 8/2009 | Krumme et al. |
| 2009/0259217 | A1 | 10/2009 | Hyde et al. |
| 2010/0286467 | A1 | 11/2010 | Pesach et al. |

FOREIGN PATENT DOCUMENTS

| EP | 0258566 | B1 | 11/1991 |
| EP | 0256694 | B1 | 7/1992 |
| EP | 0398394 | B1 | 10/1993 |
| EP | 0338671 | B1 | 5/1994 |
| EP | 0749757 | A2 | 12/1996 |
| EP | 0806738 | A1 | 11/1997 |
| EP | 0554995 | B1 | 12/1997 |
| EP | 0763368 | B1 | 2/2001 |
| EP | 0917882 | B1 | 5/2003 |
| EP | 1338295 | A1 | 8/2003 |
| EP | 0830597 | B1 | 8/2004 |
| EP | 1177802 | B1 | 9/2004 |
| EP | 1347705 | B1 | 12/2005 |
| EP | 1007137 | B1 | 1/2006 |
| EP | 1688085 | A1 | 8/2006 |
| EP | 1839694 | A1 | 10/2007 |
| EP | 1109586 | B2 | 10/2009 |
| EP | 1473050 | B1 | 12/2009 |
| EP | 1115435 | B2 | 7/2012 |
| GB | 2218831 | A | 11/1989 |
| WO | WO/1994/008647 | A1 | 4/1994 |
| WO | WO/1995/024229 | A2 | 9/1995 |
| WO | WO/1995/028878 | A1 | 11/1995 |
| WO | WO/1995/031233 | A1 | 11/1995 |
| WO | WO/1996/008281 | A1 | 3/1996 |
| WO | WO/1996/014100 | A1 | 5/1996 |
| WO | WO/1996/020745 | A1 | 7/1996 |
| WO | WO/1996/036389 | A1 | 11/1996 |
| WO | WO/1997/021456 | A1 | 6/1997 |
| WO | WO/1997/040482 | A1 | 10/1997 |
| WO | WO/1998/014234 | A1 | 4/1998 |
| WO | WO/1998/017336 | A1 | 4/1998 |
| WO | WO/1998/020439 | A1 | 5/1998 |
| WO | WO/1998/024358 | A2 | 6/1998 |
| WO | WO/1998/042407 | A1 | 10/1998 |
| WO | WO/1998/049659 | A2 | 11/1998 |
| WO | WO/1998/058693 | A1 | 12/1998 |
| WO | WO/1998/059487 | A1 | 12/1998 |
| WO | WO/1999/008183 | A1 | 2/1999 |
| WO | WO/1999/010801 | A1 | 3/1999 |
| WO | WO/1999/018532 | A1 | 4/1999 |
| WO | WO/1999/022236 | A1 | 5/1999 |
| WO | WO/1999/044655 | A2 | 9/1999 |
| WO | WO/1999/059663 | A1 | 11/1999 |
| WO | WO/2000/010628 | A2 | 3/2000 |
| WO | WO2000028217 | B1 | 8/2000 |
| WO | WO/2000/069493 | A1 | 11/2000 |
| WO | WO/2001/000261 | A1 | 1/2001 |
| WO | WO/2001/061616 | A2 | 8/2001 |
| WO | WO/2001/070304 | A1 | 9/2001 |
| WO | WO/2002/004047 | A2 | 1/2002 |
| WO | WO/2002/024257 | A1 | 3/2002 |
| WO | WO/2002/049509 | A2 | 6/2002 |
| WO | WO/2002/053220 | A2 | 7/2002 |
| WO | WO/2002/056945 | A2 | 7/2002 |
| WO | WO/2002/070049 | A1 | 9/2002 |
| WO | WO2002083209 | A9 | 12/2002 |
| WO | WO/2003/008014 | A2 | 1/2003 |
| WO | WO/2003/053498 | A2 | 7/2003 |
| WO | WO/2003/059422 | A1 | 7/2003 |
| WO | WO/2003/063932 | A2 | 8/2003 |
| WO | WO/2003/071930 | A2 | 9/2003 |
| WO | WO/2003/090838 | A1 | 11/2003 |
| WO | WO/2003/094075 | A1 | 11/2003 |
| WO | WO/2004/006981 | A2 | 1/2004 |
| WO | WO/2004/007133 | A1 | 1/2004 |
| WO | WO/2004/008956 | A2 | 1/2004 |
| WO | WO/2004/009160 | A1 | 1/2004 |
| WO | WO/2004/028596 | A1 | 4/2004 |
| WO | WO/2004/058327 | A2 | 7/2004 |
| WO | WO/2004/069095 | A2 | 8/2004 |
| WO | WO/2004/070548 | A2 | 8/2004 |
| WO | WO/2004/070557 | A2 | 8/2004 |
| WO | WO/2004/070994 | A2 | 8/2004 |
| WO | WO/2004/070995 | A2 | 8/2004 |
| WO | WO/2004/098390 | A2 | 11/2004 |
| WO | WO/2005/000378 | A2 | 1/2005 |
| WO | WO/2005/010796 | A2 | 2/2005 |
| WO | WO/2005/016411 | A2 | 2/2005 |
| WO | WO/2005/019766 | A2 | 3/2005 |
| WO | WO/2005/019987 | A2 | 3/2005 |
| WO | WO/2005/039671 | A2 | 5/2005 |
| WO | WO/2005/094920 | A1 | 10/2005 |
| WO | WO/2005/101279 | A2 | 10/2005 |
| WO | WO/2005/102416 | A1 | 11/2005 |
| WO | WO/2005/112899 | A2 | 12/2005 |
| WO | WO/2005/121938 | A2 | 12/2005 |
| WO | WO/2006/001929 | A1 | 1/2006 |
| WO | WO/2006/023147 | A2 | 3/2006 |
| WO | WO/2006/032652 | A1 | 3/2006 |
| WO | WO/2006/081975 | A1 | 8/2006 |
| WO | WO/2006/083831 | A1 | 8/2006 |
| WO | WO/2006/097453 | A1 | 9/2006 |
| WO | WO/2006/108809 | A1 | 10/2006 |
| WO | WO/2007/016145 | A1 | 2/2007 |
| WO | WO/2007/094833 | A1 | 8/2007 |
| WO | WO/2009/083600 | A1 | 7/2009 |

OTHER PUBLICATIONS

U.S. Appl. No. 14/935,874, filed Nov. 9, 2015.
U.S. Appl. No. 16/556,399, filed Aug. 30, 2019.
International Search Report and Written Opinion From Corresponding International Application No. PCT/US2007/003490, dated Nov. 28, 2007 (20 pages).
International Search Report and Written Opinion From Corresponding International Application No. PCT/US2007/003567, dated Oct. 17, 2007 (18 pages).
International Search Report and Written Opinion From Corresponding International Application No. PCT/US2007/003587, Nov. 12, 2007 (18 pages).
International Search Report and Written Opinion From Corresponding International Application No. PCT/US2007/003634, Oct. 2, 2007 (18 pages).
International Search Report From Corresponding International Application No. PCT/US2009/060158, dated Mar. 23, 2010 (7 pages).
International Search Report and Written Opinion From Corresponding International Application No. PCT/US2009/093169, dated Mar. 31, 2010 (23 pages).
International Preliminary Report on Patentability From Corresponding International Application No. PCT/US2007/003567, dated Aug. 21, 2008 (11 pages).
Extended European Search Report From European Application No. 09075460.7, dated Mar. 5, 2010 (14 pages).
Office Action from Japanese Appln. No. 2002-591067 dated Jun. 10, 2008 (4 pages).
Non-final Office Action from corresponding U.S. Appl. No. 12/249,891, dated Nov. 18, 2009 (15 pages).
Conical fittings with a 6% (Luer) taper for syringes, needles and certain other medical equipment—Lock fittings, British Standard, BS EN 1707 : 1997 (20 pages).
Conical fittings with a 6% (Luer) taper for syringes, needles and certain other medical equipment, Part 1. General requirements, British Standard, BS EN 20594-1 : 1994 ISO 594-1 : 1986 (17 pages).
A Preliminary Report on Patentability from corresponding International Appln. No. PCT/US2011/022051 dated Jul. 24, 2012 (13 pages).

(56)       References Cited

OTHER PUBLICATIONS

Search Report from corresponding EP Appln. No. 10075446.4 dated Aug. 25, 2011 (10 pages).
Search Report from corresponding International Appln. No. PCT/US2011/030553 dated Dec. 23, 2011 (12 pages).

* cited by examiner

<u>18</u>

SYSTEM AND METHOD FOR ADMINISTERING AN INFUSIBLE FLUID

CROSS REFERENCE TO RELATED APPLICATIONS

This application is a continuation of U.S. patent application Ser. No. 16/556,399 filed on Aug. 30, 2019, which is a continuation of U.S. patent application Ser. No. 14/935,874 filed on Nov. 9, 2015, which is a continuation of U.S. patent application Ser. No. 12/249,636 filed on Oct. 10, 2008, each of which is hereby incorporated by reference herein in its entirety.

TECHNICAL FIELD

This disclosure relates to infusion pump assemblies and, more particularly, to infusion pump assemblies configured to administer sequential, multi-part, infusion events and one-time infusion events.

BACKGROUND

An infusion pump assembly may be used to infuse a fluid (e.g., a medication or nutrient) into a user. The fluid may be infused intravenously (i.e., into a vein), subcutaneously (i.e., into the skin), arterially (i.e., into an artery), and epidurally (i.e., into the epidural space).

Infusion pump assemblies may administer fluids in ways that would be impractically expensive/unreliable if performed manually by nursing staff. For example, an infusion pump assembly may repeatedly administer small quantities of an infusible fluid (e.g., 0.1 mL per hour), while allowing the user to request one-time larger "bolus" doses.

SUMMARY OF DISCLOSURE

In a first implementation, a method includes administering a sequential, multi-part, infusion event, wherein the sequential, multi-part, infusion event includes a plurality of discrete infusion events. If a one-time infusion event is available to be administered, the administration of at least a portion of the plurality of discrete infusion events included within the sequential, multi-part, infusion event is delayed. The one-time infusion event is administered.

One or more of the following features may be included. Once the administration of the one-time infusion event is completed, the at least a portion of the plurality of discrete infusion events included within the sequential, multi-part, infusion event may be administered. The sequential, multi-part, infusion event may include a basal infusion event. The sequential, multi-part, infusion event may include an extended bolus infusion event. The one-time infusion event may include a normal bolus infusion event.

At least one of the plurality of discrete infusion events may include a plurality of discrete infusion sub-events. The one-time infusion event may include a plurality of one-time infusion sub-events.

In another implementation, a computer program product resides on a computer readable medium that has a plurality of instructions stored on it. When executed by a processor, the instructions cause the processor to perform operations including administering a sequential, multi-part, infusion event, wherein the sequential, multi-part, infusion event includes a plurality of discrete infusion events. If a one-time infusion event is available to be administered, the administration of at least a portion of the plurality of discrete infusion events included within the sequential, multi-part, infusion event is delayed. The one-time infusion event is administered.

One or more of the following features may be included. Once the administration of the one-time infusion event is completed, the at least a portion of the plurality of discrete infusion events included within the sequential, multi-part, infusion event may be administered. The sequential, multi-part, infusion event may include a basal infusion event. The sequential, multi-part, infusion event may include an extended bolus infusion event. The one-time infusion event may include a normal bolus infusion event.

At least one of the plurality of discrete infusion events may include a plurality of discrete infusion sub-events. The one-time infusion event may include a plurality of one-time infusion sub-events.

In another implementation, an infusion pump assembly is configured to perform operations including administering a sequential, multi-part, infusion event, wherein the sequential, multi-part, infusion event includes a plurality of discrete infusion events. If a one-time infusion event is available to be administered, the administration of at least a portion of the plurality of discrete infusion events included within the sequential, multi-part, infusion event is delayed. The one-time infusion event is administered.

One or more of the following features may be included. Once the administration of the one-time infusion event is completed, the at least a portion of the plurality of discrete infusion events included within the sequential, multi-part, infusion event may be administered. The sequential, multi-part, infusion event may include a basal infusion event. The sequential, multi-part, infusion event may include an extended bolus infusion event. The one-time infusion event may include a normal bolus infusion event.

At least one of the plurality of discrete infusion events may include a plurality of discrete infusion sub-events. The one-time infusion event may include a plurality of one-time infusion sub-events.

The details of one or more implementations are set forth in the accompanying drawings and the description below. Other features and advantages will become apparent from the description, the drawings, and the claims.

BRIEF DESCRIPTION OF THE DRAWINGS

Like reference symbols in the various drawings indicate like elements.

DETAILED DESCRIPTION OF THE PREFERRED EMBODIMENTS

Figure 1:
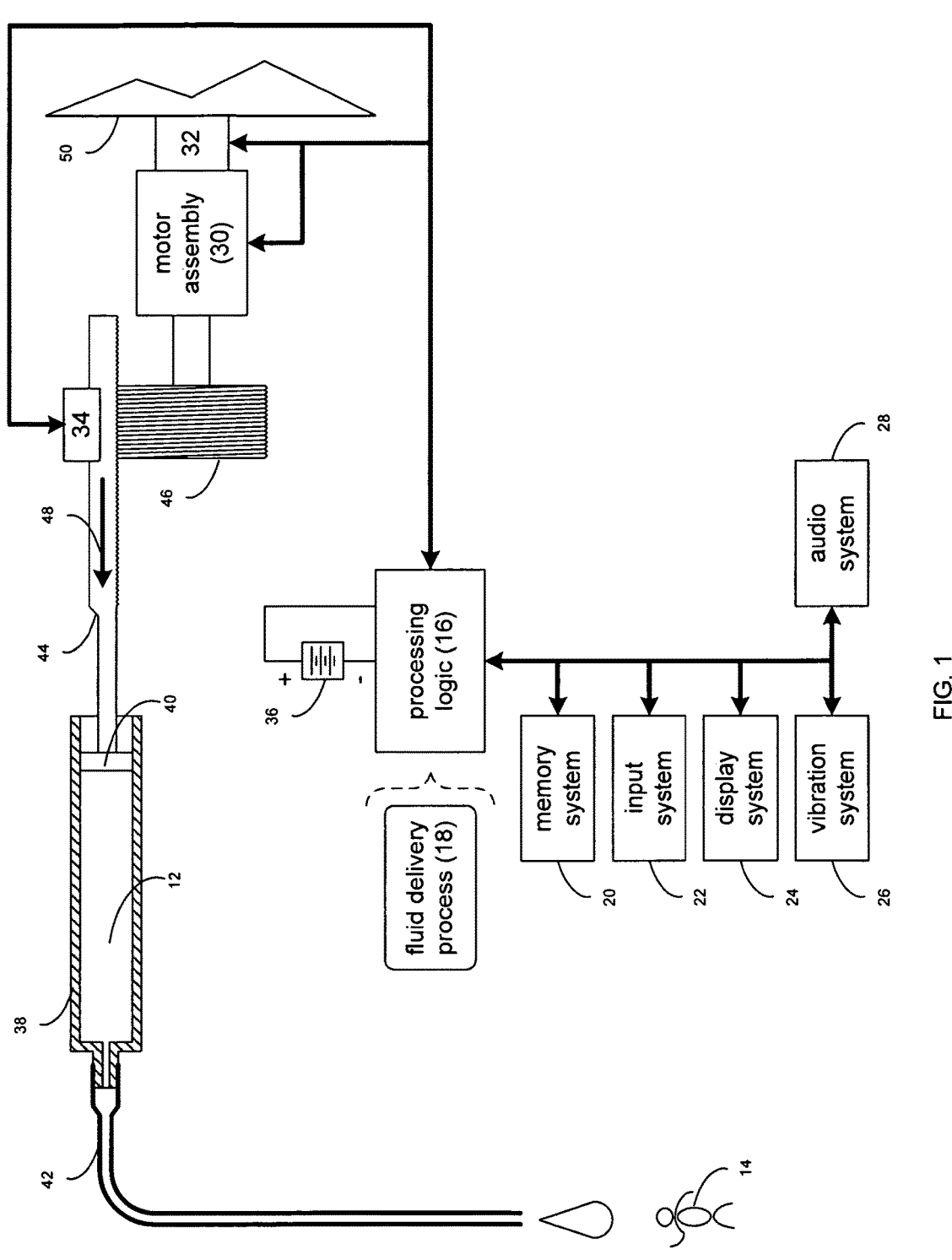
FIG. 1 is a diagrammatic view of an infusion pump assembly executing a fluid delivery process.

Referring to FIG. 1, there is shown in infusion pump assembly 10 that may be configured to deliver infusible fluid 12 to user 14. As discussed above, infusible fluid 12 may be delivered intravenously (i.e., into a vein), subcutaneously (i.e., into the skin), arterially (i.e., into an artery), and epidurally (i.e., into the epidural space). Examples of infusible fluid 12 may include but are not limited to insulin, nutrients, saline solution, antibiotics, analgesics, anesthetics, hormones, vasoactive drugs, and chelation drugs Infusion pump assembly 10 may include processing logic 16 that executes one or more processes that may be required for infusion pump assembly 10 to operate properly. Processing logic 16 may include one or more microprocessors (not shown), one or more input/output controllers (not shown), and cache memory devices (not shown). One or more data buses and/or memory buses may be used to interconnect processing logic 16 with one or more subsystems.

Processing logic 16 may execute fluid delivery process 18 that (as will be discussed below in greater detail) may delay the administration of at least a portion of a sequential, multi-part, infusion event until a one-time infusion event is completely administered.

Examples of the subsystems interconnected with processing logic 16 may include but are not limited to memory system 20, input system 22, display system 24, vibration system 26, audio system 28, motor assembly 30, force sensor 32, and displacement detection device 34. Infusion pump assembly 10 may include primary power supply 36 (e.g. a primary battery) for providing electrical power to at least a portion of processing logic 16 and one or more of the subsystems (e.g., memory system 20, input system 22, display system 24, vibration system 26, audio system 28, motor assembly 30, force sensor 32, and displacement detection device 34).

The instruction sets and subroutines of fluid delivery process 18, which may be stored on a storage device (e.g., memory system 20) accessible by processing logic 16, may be executed by one or more processors (not shown) and one or more memory architectures (e.g., memory system 20) included within infusion pump assembly 10. Examples of memory system 20 may include but are not limited to: a random access memory; a read-only memory; and a flash memory.

Infusion pump assembly 10 may include reservoir assembly 38 configured to contain infusible fluid 12. In some embodiments, the reservoir assembly 38 may be a reservoir assembly similar to that described in U.S. Patent Application No. US 2004-0135078-A1, published Jul. 15, 2004, which is herein incorporated by reference in its entirety. In other embodiments, the reservoir assembly may be any assembly in which fluid may be acted upon such that at least a portion of the fluid may flow out of the reservoir assembly, for example, the reservoir assembly, in various embodiments, may include but is not limited to: a barrel with a plunger, a cassette or a container at least partially constructed of a flexible membrane.

Plunger assembly 40 may be configured to displace infusible fluid 12 from reservoir assembly 38 through cannula assembly 42 so that infusible fluid 12 may be delivered to user 14. In this particular embodiment, plunger assembly 40 is shown to be displaceable by partial nut assembly 44, which may engage lead screw assembly 46 that may be rotatable by motor assembly 30 in response to signals received from processing logic 16. In this particular embodiment, the combination of motor assembly 30, plunger assembly 40, partial nut assembly 44, and lead screw assembly 46 may form a pump assembly that effectuates the dispensing of infusible fluid 12 contained within reservoir assembly 38. An example of partial nut assembly 44 may include but is not limited to a nut assembly that is configured to wrap around lead screw assembly 46 by e.g., 30 degrees. In some embodiments, the pump assembly may be similar to one described in U.S. Pat. No. 7,306,578, issued Dec. 11, 2007, which is herein incorporated by reference in its entirety.

During operation of infusion pump assembly 10, infusible fluid 12 may be delivered to user 14 in accordance with e.g. a defined delivery schedule. For illustrative purposes only, assume that infusion pump assembly 10 is configured to provide 0.00025 mL of infusible fluid 12 to user 14 every three minutes. Accordingly, every three minutes, processing logic 16 may provide the appropriate drive signals to motor assembly 30 to allow motor assembly 30 to rotate lead screw assembly 46 the appropriate amount so that partial nut assembly 44 (and therefore plunger assembly 40) may be displaced the appropriate amount in the direction of arrow 48 so that 0.00025 mL of infusible fluid 12 are provided to user 14 (via cannula 42). It should be understood that the volume of infusible fluid 12 that may be provided to user 14 may vary based upon, at least in part, the nature of the infusible fluid (e.g., the type of fluid, concentration, etc.), use parameters (e.g., treatment type, dosage, etc.), as well as various other factors that will be understood by one having skill in the art. As such, the foregoing illustrative example should not be construed as a limitation of the present disclosure.

Force sensor 32 may be configured to provide processing logic 16 with data concerning the force required to drive plunger assembly 40 into reservoir assembly 38. Force sensor 32 may include one or more strain gauges and/or pressure sensing gauges and may be positioned between motor assembly 30 and an immovable object (e.g. bracket assembly 50) included within infusion pump assembly 10.

In one embodiment, force sensor 32 includes four strain gauges (not shown), such that: two of the four strain gauges are configured to be compressed when driving plunger 40 into reservoir assembly 38; and two of the four strain gauges are configured to be stretched when driving plunger 40 into reservoir assembly 38. The four strain gauges (not shown) may be connected to a Wheatstone Bridge (not shown) that produces an analog force signal (not shown) that is a function of the pressure sensed by force sensor 32. The analog force signal (not shown) produced by force sensor 32 may be provided to an analog-to-digital converter (not shown) that may convert the analog force signal (not shown) into a digital force signal (not shown) that may be provided to processing logic 16. An amplifier assembly (not shown) may be positioned prior to the above-described analog-to-digital converter and may be configured to amplify the output of e.g., force sensor 32 to a level sufficient to be processed by the above-described analog-to-digital converter.

Motor assembly 30 may be configured as e.g., a brush-type DC electric motor. Further, motor assembly 30 may include a reduction gear assembly (not shown) that e.g. requires motor assembly 30 to rotate e.g., three-thousand revolutions for each revolution of lead screw assembly 42, thus increasing the torque and resolution of motor assembly 30 by a factor of three-thousand.

As discussed above, infusion pump assembly 10 may be configured to deliver infusible fluid 12 to user 14. Infusible fluid 12 may be delivered to user 14 via one or more different infusion event types. For example, infusion pump assembly 10 may deliver infusible fluid 12 via may a sequential, multi-part, infusion event (that may include a plurality of discrete infusion events) and/or a one-time infusion event.

Examples of such a sequential, multi-part, infusion event may include but are not limited to a basal infusion event and an extended-bolus infusion event. As is known in the art, a basal infusion event refers to the repeated injection of small (e.g. 0.05 unit) quantities of infusible fluid 12 at a predefined interval (e.g. every three minutes) that may be repeated indefinitely. Further, the basal infusion rates may be pre-programmed and may include specified rates for pre-pro-grammed time-frames, e.g., a rate of 0.50 units per hour from 6 am-3 pm; a rate of 0.40 units per hour from 3 pm-10 pm; and a rate of 0.35 units per hour from 10 pm-6 am. However, similarly, the basal rate may be 0.025 units per hour, and may not change according to pre-programmed time-frames. The basal rates may be repeated regularly/daily until otherwise changed.

Further and as is known in the art, an extended-bolus infusion event may refer to the repeated injection of small (e.g. 0.05 unit) quantities of infusible fluid 12 at a predefined interval (e.g. every three minutes) that is repeated for a defined number of intervals (e.g., three intervals) or for a defined period of time (e.g., nine minutes). An extended-bolus infusion event may occur simultaneously with a basal infusion event.

Figure 2:
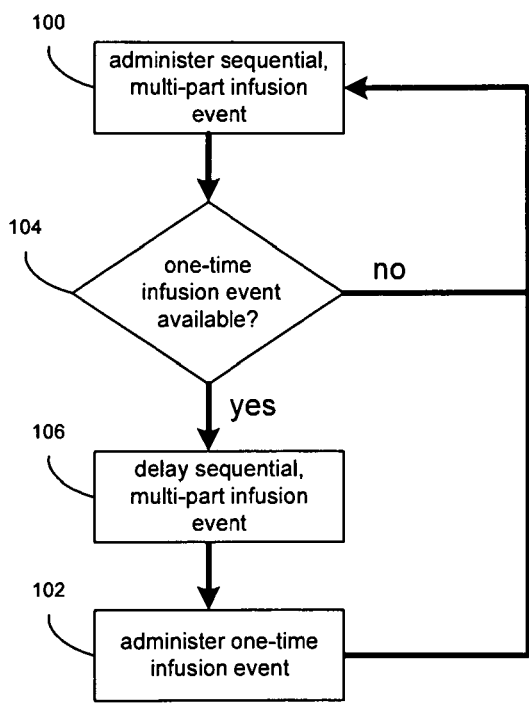
FIG. 2 is a flowchart of the fluid delivery process of FIG. 1.
Figure 3:
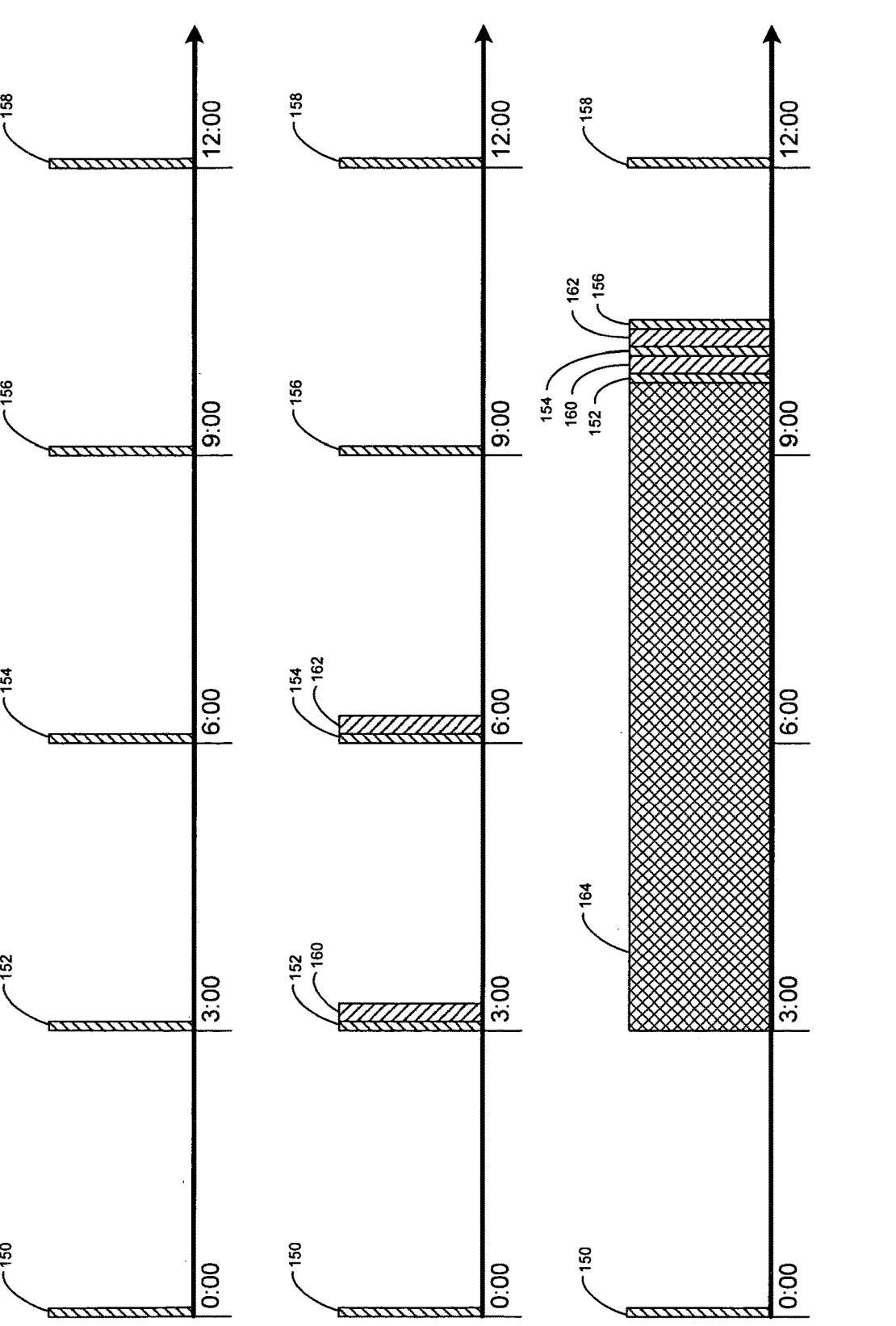
FIG. 3 is a timeline illustrative of a plurality of discrete infusion events.

Referring also to FIGS. 2-3, assume for illustrative pur-poses only that user 14 configures infusion pump assembly 10 to administer a basal dose (e.g. 0.05 units) of infusible fluid 12 every three minutes. As discussed above, infusion pump assembly 10 may include input system 22 and display system 24.

Accordingly, user 14 may utilize input system 22 to define a basal infusion event for infusible fluid 12 (e.g., 1.00 units per hour), which may be confirmed via display system 24. While, in this example, the basal infusion event is described as 1.00 units per hour, this is for illustrative purposes only and is not intended to be a limitation of this disclosure, as either or both of the unit quantity and time period may be adjusted upward or downward. Infusion pump assembly 10 may then determine an infusion schedule based upon the basal infusion event defined; and may administer 100 infus-ible fluid 12. For example, infusion pump assembly 10 may deliver 0.05 units of infusible fluid 12 every three minutes, resulting in the delivery of the basal dose of infusible fluid 12 defined by the user (i.e., 1.00 units per hour).

Once defined and/or confirmed, fluid delivery process 18 may administer 100 the sequential, multi-part, infusion event (e.g., 0.05 units of infusible fluid 12 every three minutes). Accordingly, while administering 100 the sequen-tial, multi-part, infusion event, infusion pump assembly 10: may infuse a first 0.05 unit dose 150 of infusible fluid 12 at t=0:00 (i.e., a first discrete infusion event), may infuse a second 0.05 unit dose 152 of infusible fluid 12 at t=3:00 (i.e., a second discrete infusion event); may infuse a third 0.05 unit dose 154 of infusible fluid 12 at t=6:00 (i.e., a third discrete infusion event); may infuse a fourth 0.05 unit dose 156 of infusible fluid 12 at t=9:00 (i.e., a fourth discrete infusion event); and may infuse a fifth 0.05 unit dose 158 of infusible fluid 12 at t=12:00 (i.e., a fifth discrete infusion event). As discussed above, this pattern of infusing 0.05 unit doses of infusible fluid 12 every three minutes may be repeated indefinitely in this example, as this is an illustrative example of a basal infusion event.

Further, assume for illustrative purposes that infusible fluid 12 is insulin and sometime after the first 0.05 unit dose 150 of infusible fluid 12 is administered 100 by fluid delivery process 18 (but before the second 0.05 unit dose 150 of infusible fluid 12 is administered 100 by fluid delivery process 18), user 14 checks their blood glucose level and realizes that their blood glucose level is running a little higher than normal. Accordingly, user 14 may define an extended bolus infusion event via fluid delivery process 18.

An extended bolus infusion event may refer to the continu-ous infusion of a defined quantity of infusible fluid 12 over a finite period of time. However, as such an infusion methodology is impractical/undesirable for an infusion pump assembly, when administered by such an infusion pump assembly, an extended bolus infusion event may refer to the infusion of additional small doses of infusible fluid 12 over a finite period of time.

Accordingly, user 14 may utilize input system 22 to define an extended bolus infusion event for infusible fluid 12 (e.g., 0.20 units over the next six minutes), which may be con-firmed via display system 24. While, in this example, the extended bolus infusion event is described as 0.20 units over the next six minutes, this is for illustrative purposes only and is not intended to be a limitation of this disclosure, as either or both of the unit quantity and total time interval may be adjusted upward or downward. Once defined and/or con-firmed, fluid delivery process 18 may determine an infusion schedule based upon the extended bolus infusion event defined; and may administer 100 infusible fluid 12. For example, infusion pump assembly 10 may deliver 0.10 units of infusible fluid 12 every three minutes for the next two interval cycles (or six minutes), resulting in the delivery of the extended bolus dose of infusible fluid 12 defined by the user (i.e., units over the next six minutes).

Accordingly, while administering 100 the second, sequen-tial, multi-part, infusion event, infusion pump assembly 10 may infuse a first 0.10 unit dose 160 of infusible fluid 12 at t=3:00 (e.g., after administering the second 0.05 unit dose 152 of infusible fluid 12). Infusion pump assembly 10 may also infuse a second unit dose 162 of infusible fluid 12 at t=6:00 (e.g., after administering the third unit dose 154 of infusible fluid 12).

Assume for illustrative purposes only that after user 14 programs infusion pump assembly 10 to administer 100 the first sequential, multi-part, infusion event (i.e., 0.05 units infused every three minute interval repeated continuously) and administer 100 the second sequential, multi-part, infu-sion event (i.e., 0.10 units infused every three minute interval for two intervals), user 14 decides to eat a very large meal. Predicting that their blood glucose level might increase considerably, user 14 may program infusion pump assembly 10 (via input system 22 and/or display system 24) to administer 102 a one-time infusion event. An example of such a one-time infusion event may include but is not limited to a normal bolus infusion event. As is known in the art, a normal bolus infusion event refers to a one-time infusion of infusible fluid 12.

For illustrative purposes only, assume that user 14 wishes to have infusion pump assembly 10 administer 102 a bolus dose of thirty-six units of infusible fluid 12. Fluid delivery process 18 may monitor the various infusion events being administered by fluid delivery process 18 to determine 104 whether a one-time infusion event is available to be admin-istered. If 104 a one-time infusion event is available for administration 102, fluid delivery process 10 may delay 106 the administration of at least a portion of the sequential, multi-part, infusion event.

Continuing with the above-stated example, once user 14 completes the programming of fluid delivery process 18 to deliver one-time infusion event 164 (i.e., the thirty-six unit bolus dose of infusible fluid 12), upon fluid delivery process 18 determining 104 that the one-time infusion event is available for administration 102, fluid delivery process 18 may delay 106 the administration 100 of each sequential, multi-part infusion event and administer 102 the available one-time infusion event.

Specifically and as discussed above, prior to user 14 programming fluid delivery process 18 to deliver one-time infusion event 164, infusion delivery process 18 was administering 100 a first sequential, multi-part, infusion event (i.e., 0.05 units infused every three minute interval repeated continuously) and administering 100 a second sequential, multi-part, infusion event (i.e., 0.10 units infused every three minute interval for two intervals).

For illustrative purposes only, the first sequential, multi-part, infusion event may be represented within FIG. 3 as 0.05 unit dose 150 @ t=0:00, 0.05 unit dose 152 @ t=3:00, 0.05 unit dose 154 @ t=6:00, 0.05 unit dose 156 @ t=9:00, and unit dose 158 @ t=12:00. As the first sequential, multi-part, infusion event as described above is a basal infusion event, infusion pump assembly 10 (in conjunction with fluid delivery process 18) may continue to infuse 0.05 unit doses of infusible fluid 12 at three minute intervals indefinitely (i.e., until the procedure is cancelled by user 14).

Further and for illustrative purposes only, the second sequential, multi-part, infusion event may be represented within FIG. 3 as 0.10 unit dose 160 @ t=3:00 and 0.10 unit dose 162 @ t=6:00. As the second sequential, multi-part, infusion event is described above as an extended bolus infusion event, infusion pump assembly 10 (in conjunction with fluid delivery process 18) may continue to infuse 0.10 unit doses of infusible fluid 12 at three minute intervals for exactly two intervals (i.e., the number of intervals defined by user 14).

Continuing with the above-stated example, upon fluid delivery process 18 determining 104 that the thirty-six unit normal bolus dose of infusible fluid 12 (i.e., one-time infusion event 164) is available for administration 102, fluid delivery process 18 may delay 106 the administration 100 of each sequential, multi-part infusion event and may start administering 102 one-time infusion event 164 that is available for administration.

Accordingly and for illustrative purposes only, assume that upon completion of the programming of infusion pump assembly 10 to deliver the thirty-six unit normal bolus does of infusible fluid 12 (i.e., the one-time infusion event), fluid delivery process begins administering 102 one-time infusion event 164. Being that one-time infusion event 164 is comparatively large, it may take longer than three minutes (i.e., the time interval between individual infused doses of the sequential, multi-part, infusion events), one or more of the individual infused doses of the sequential, multi-part, infusion events may need to be delayed.

Specifically, assume that it will take infusion pump assembly 10 greater than six minutes to infuse thirty-six units of infusible fluid 12. Accordingly, fluid delivery process 18 may delay 0.05 unit dose 152 (i.e., scheduled to be infused @ t=3:00), 0.05 unit dose 154 (i.e., scheduled to be infused @ t=6:00), and 0.05 unit dose 156 (i.e., scheduled to be infused @ t=9:00) until after one-time infusion event 164 (i.e., the thirty-six unit normal bolus dose of infusible fluid 12) is completely administered. Further, fluid delivery process 18 may delay 0.10 unit dose 160 (i.e., scheduled to be infused @ t=3:00 and 0.10 unit dose 162 (i.e., scheduled to be infused @ t=6:00) until after one-time infusion event 164.

Once administration 102 of one-time infusion event 164 is completed by fluid delivery process 18, any discrete infusion events included within the sequential, multi-part, infusion event that were delayed may be administered 100 by fluid delivery process 18.

Accordingly, once one-time infusion event 164 (i.e., the thirty-six unit normal bolus dose of infusible fluid 12) is completely administered 102, fluid delivery process 18 may administer 100 0.05 unit dose 152, 0.05 unit dose 154, 0.05 unit dose 156, 0.10 unit dose 160, and 0.10 unit dose 162.

While fluid delivery process 18 is shown to administer 100 0.05 unit dose 152, then 0.10 unit dose 160, then 0.05 unit dose 154, then 0.10 unit dose 162, and then 0.05 unit dose 156, this is for illustrative purposes only and is not intended to be a limitation of this disclosure, as other configurations are possible and are considered to be within the scope of this disclosure. For example, upon fluid delivery process 18 completing the administration 102 of one-time infusion event 164 (i.e., the thirty-six unit normal bolus dose of infusible fluid 12), fluid delivery process 18 may administer 100 all of the delayed discrete infusion events associated with the first sequential, multi-part infusion event (i.e., namely unit dose 152, 0.05 unit dose 154, and 0.05 unit dose 156. Fluid delivery process 18 may then administer 100 all of the delayed discrete infusion events associated with the second sequential, multi-part infusion event (i.e., 0.10 unit dose 160, and 0.10 unit dose 162).

While one-time infusion event 164 (i.e., the thirty-six unit normal bolus dose of infusible fluid 12) is shown as being infused beginning at t=3:00, this is for illustrative purposes only and is not intended to be a limitation of this disclosure. Specifically, fluid delivery process 18 may not need to begin infusing one-time infusion event 164 at one of the three-minute intervals (e.g., t=0:00, t=3:00, t=6:00, t=9:00, or t=12:00) and may begin administering 102 one-time infusion event 164 at any time.

While each discrete infusion event (e.g., 0.05 unit dose 152, 0.05 unit dose 154, 0.05 unit dose 156, 0.10 unit dose 160, and 0.10 unit dose 162) and one-time infusion event 164 are shown as being a single event, this is for illustrative purposes only and is not intended to be a limitation of this disclosure. Specifically, at least one of the plurality of discrete infusion events e.g., 0.05 unit dose 152, 0.05 unit dose 154, 0.05 unit dose 156, 0.10 unit dose 160, and 0.10 unit dose 162) may include a plurality of discrete infusion sub-events. Further, one-time infusion event 164 may include a plurality of one-time infusion sub-events.

Figure 4:
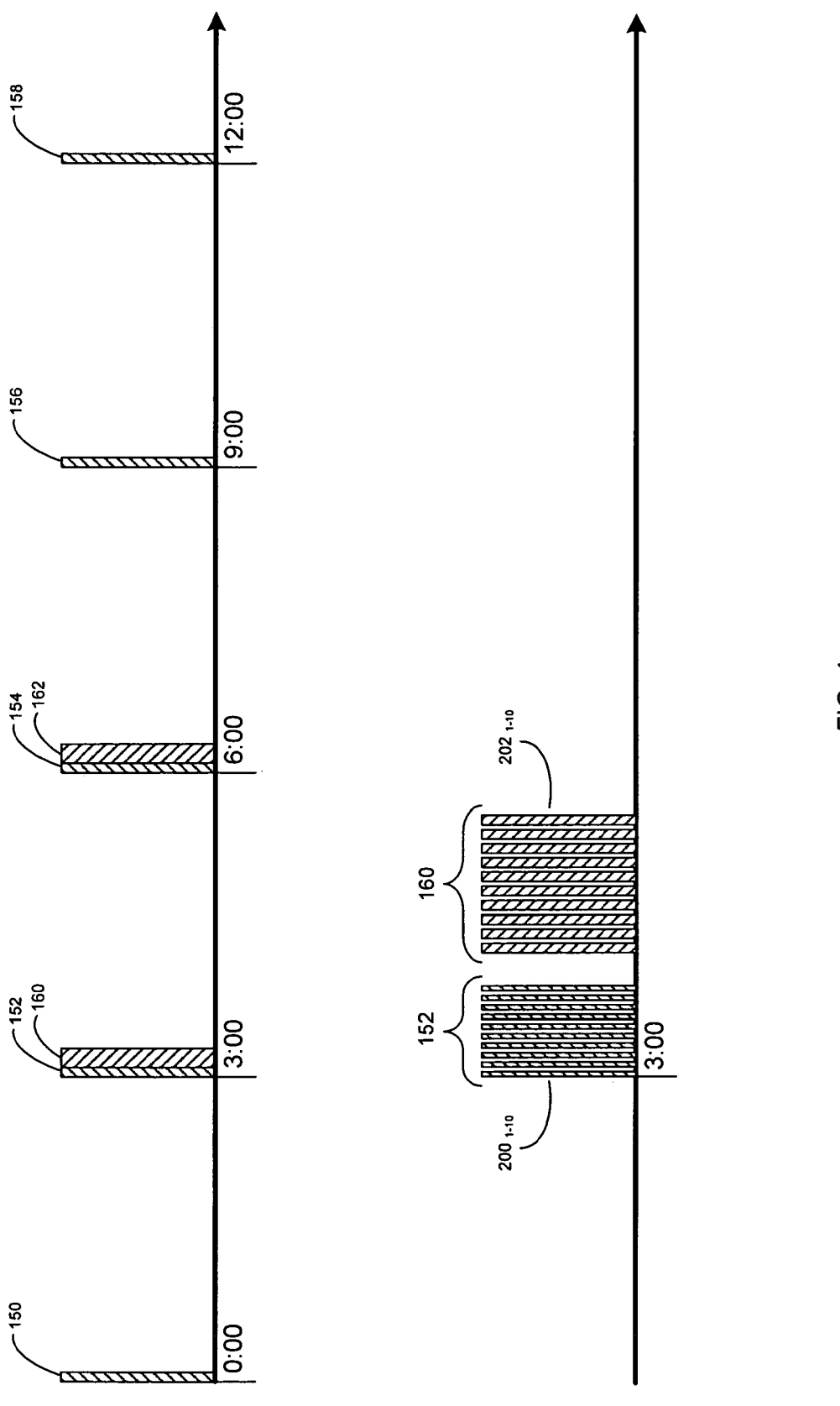
FIG. 4 is a more detailed view of two discrete infusion events included within FIG. 3.

Referring also to FIG. 4 and for illustrative purposes, 0.05 unit dose 152 is shown to include ten discrete infusion sub-events (e.g., infusion sub-events $200_{1-10}$), wherein a 0.005 unit dose of infusible fluid 12 is infused during each of the ten discrete infusion sub-events. Additionally, 0.10 unit dose 160 is shown to include ten discrete infusion sub-events (e.g., infusion sub-events $202_{1-10}$), wherein a 0.01 unit dose of infusible fluid 12 is delivered during each of the ten discrete infusion sub-events. Further, one-time infusion event 164 may include e.g., 360 one-time infusion sub-events (not shown), wherein a 0.1 unit dose of infusible fluid 12 is delivered during each of the 360 one-time infusion sub-events. The number of sub-events defined above and the quantity of infusible fluid 12 delivered during each sub-event is solely for illustrative purposes only and is not intended to be a limitation of this disclosure, as the number of sub-events and/or the quantity of infusible fluid 12 delivered during each sub-event may be increased or decreased depending upon e.g., the design criteria of infusion pump assembly 10 and/or the implementation of fluid delivery process 18.

Before, after, or in between the above-described infusion sub-events, infusion pump assembly 10 may confirm the proper operation of infusion pump assembly 10 through the use of e.g., force sensor 32 (i.e., which may determine the occurrence of an occlusion) and displacement detection device 34 (i.e., which may determine the occurrence of a mechanical failure).

A number of implementations have been described. Nevertheless, it will be understood that various modifications may be made. Accordingly, other implementations are within the scope of the following claims.

What is claimed is:

1. An infusion pump assembly comprising a processor including processing logic configured to perform operations comprising:

administering a sequential, multi-part, infusion event, wherein the sequential, multi-part, infusion event includes a plurality of discrete infusion events;

determining that a one-time infusion event is available to be administered;

after the determining that the one-time infusion event is available to be administered, delaying the administration of at least a portion of the plurality of discrete infusion events included within the sequential, multi-part, infusion event; and administering the one-time infusion event;

administering the delayed discrete infusion events after completion of the one-time infusion event; and resuming administration of the sequential, multi-part, infusion event at the defined time interval at the end of the duration of the one-time infusion event.

2. The infusion pump assembly of claim 1 wherein the sequential, multi-part, infusion event includes a basal infusion event.

3. The infusion pump assembly of claim 1 wherein the sequential, multi-part, infusion event includes an extended bolus infusion event.

4. The infusion pump assembly of claim 1 wherein the one-time infusion event includes a normal bolus infusion event.

5. The infusion pump assembly of claim 1 wherein at least one of the plurality of discrete infusion events includes a plurality of discrete infusion sub-events.

* * * * *